United States Patent [19]
Nalewajek et al.

[11] Patent Number: 6,133,472
[45] Date of Patent: Oct. 17, 2000

[54] FLUORINATED OXYVINYL COMPOUNDS AND METHODS OF PREPARING AND USING SAME

[75] Inventors: David Nalewajek; David Bradley; John Schabel, all of Erie County, N.Y.; Robert Blomquist, Morris County, N.J.

[73] Assignee: AlliedSignal Inc., Morristown, N.J.

[21] Appl. No.: 09/009,110

[22] Filed: Jan. 20, 1998

[51] Int. Cl.[7] .................................................. C07C 69/00
[52] U.S. Cl. ...................... 560/129; 554/225; 560/227; 560/228; 568/674; 568/669; 568/670
[58] Field of Search ............................ 554/225; 560/129, 560/227, 228; 568/674, 669, 670

[56] References Cited

U.S. PATENT DOCUMENTS

| | | | |
|---|---|---|---|
| 2,732,370 | 1/1956 | Codding | 260/91.1 |
| 3,504,016 | 3/1970 | Smeltz | 260/475 |
| 5,054,872 | 10/1991 | Fan et al. | 385/130 |
| 5,274,174 | 12/1993 | Shah et al. | 560/130 |
| 5,511,142 | 4/1996 | Horie et al. | 385/129 |

OTHER PUBLICATIONS

CA 113:25067 (1990).
B.M. Monroe, et al., "Polymers for Lightwave and Integrated Optics, Technology and Applications", L.A. Hornack, ed., p. 145, Dekker, 1992.
T. Kaino, "Polymers for Lightwave and Integrated Optics, Technology and Applications", L.A. Hornack, ed., p. 1, Dekker, 1992.

*Primary Examiner*—Paul J. Killos
*Attorney, Agent, or Firm*—Colleen Szuch

[57] ABSTRACT

Fluorine containing oxyvinyl compounds characterized by having one or more oxyvinyl groups separated from fluorine containing groups by at least one alkylene group having 2–8 carbon atoms and by at least one oxygen atom in addition to the oxygen on the oxyvinyl. In general the compounds of the invention have the generic formula:

$$Rz(L)_a(Ry)_b OROCH=CH_2.$$

Where L is $=CHCOOROCH=CH_2$; a is number of 0 to about 1; $R_y$ is $-CO-$; b is a number of 0 to about 1; R is cycloalkane or $(CH_2)_x-$, where x is a number of about 2 through about 10; $R_z$ is $R_f C_n H_m$ where $R_f$ is a fluorinated alkylene moiety of about 1 to about 12 carbon atoms which may be linear or branch chained and may contain a further $-OROCH=CH_2$ group; n is an integer of about 1 through about 6; and m is an integer of n to 2n. The compounds are suitable for use in optical devices such as fibers and waveguides, are readily radiation curable and curable by other means, and can be formulated to be of low viscosity when applied. The compounds are also suited for coatings, inks and adhesive and other applications. The invention includes methods for preparing and using the compounds and products employing the compounds. Intermediates to prepare the compounds and methods to prepare the intermediates are also included.

17 Claims, No Drawings

FLUORINATED OXYVINYL COMPOUNDS AND METHODS OF PREPARING AND USING SAME

BACKGROUND OF THE INVENTION

This invention relates to vinyl ethers which are extremely reactive monomers, known to undergo polymerization either by a cationic or a free radical mechanism and are useful in applications which require a high speed curing of a resin formulation. Vinyl ethers react much faster than the epoxy resins and therefore may be used for such applications as printing inks, coatings, elastomers, foams and other types of products dependent upon the ability of the resin to cure at a rate which is consistent with other processing steps.

This invention relates to fluorinated vinyl ethers and more particularly relates to such fluorinated compounds containing one or more oxyvinyl groups. "Oxyvinyl group" as used herein means a vinyl group connected to the remainder of the compound through an ether oxygen atom.

Some fluorinated chemical compounds are known in the art which contain oxyvinyl groups such as are described in U.S. Pat. No. 2,732,370 under the generic formula $C_nF_{2n+1}CH_2$—O—CH=$CH_2$. The compounds F—$(CF_2)_3$—$CH_2$——O—CH=$CH_2$ and F—$(CF_2)_3$——O—CH=$CH_2$ are commercially available from the company "Monomer-Polymer & Dajac". The foregoing known compounds have fluorinated structures near the oxyvinyl group and are thus believed either not to be radiation curable or not to have radiation curable reactivities to the extent desired. Further, due to the heavily fluorinated structure, adherence to substrates and compatibility with solvents and cosolutes may not be as good as desired.

Continuing development of a new coatings has led to the need for improving performance in certain applications. Such improvements can include control of flexibility, hardness, moisture resistance, and low surface energy.

One known methodology used to modify the properties of coating materials is to employ nonionic fluorochemical surfactants. These surfactants have been shown to achieve lower surface tension. It is also known to those skilled in the art, that the use of additives which are not inherently bonded in the matrix of the resin can result in decreased performance as a function of time due to migration or removal as a natural consequence of abrasion or handling. There is therefore a need for a chemically bonded material which can impart novel characteristics to resins, without loss of activity, and which is chemically miscible with the components of a matrix under investigation.

The use of photocuring technology has grown rapidly within the last decade. Photocuring involves the radiation induced polymerization or crosslinking of monomers into a three dimensional network. Photocuring has a number of advantages including: a 100% conversion to a solid composition, short cycle times and limited space and capital requirements.

Photocuring technology has been applied in planar waveguide applications. See, B. M. Monroe and W. K. Smothers, in Polymers for Lightwave and Integrated Optics, Technology and Applications, L. A. Hornak, ed., p. 145, Dekker, 1992. In its simplest application, a photocurable composition is applied to a substrate and irradiated with light in a predetermined pattern to produce (the light transmissive) or waveguide portion on the substrate. Photocuring permits one to record fine patterns (<1 μm) directly with light. The refractive index difference between the substrate and the light transmissive portion of the substrate can be controlled by either regulating the photocurable composition or the developing conditions.

Because of the dramatic growth in the telecommunications industry there is a need to develop photocurable compositions for optical waveguide and interconnect applications. In order to be useful in these applications, the photocurable composition must be highly transparent at the working wavelength and possess low intrinsic absorption and scattering loss. Unfortunately, in the near-infrared region, among which the 1300 and the 1550 nm wavelengths are preferred for optical communications, conventional photocurable materials possess neither the required transparency or low intrinsic absorption loss.

The absorption loss in the near-infrared stems from the high harmonics of bond vibrations of the C—H bonds which comprise the basic molecules in conventional acrylate photopolymers. One way to shift the absorption bands to higher wavelengths, is to replace most, if not all, of the hydrogen atoms in the conventional materials with heavier elements such as deuterium, fluorine, and chlorine; e.g. as described by T. Kaino, in Polymers for Lightwave and Integrated Optics, Technology and Applications, L. A. Hornak, ed., p. 1, Dekker, 1992. The replacement of hydrogen atoms with fluorine atoms is the easiest of these methods. It is known in the art that optical loss at 1300 and 1550 nm can be significantly reduced by increasing the fluorine to hydrogen ratio in the polymer. It has been reported that some perfluorinated polyimide polymers have very low absorption over the wavelengths used in optical communications. See, S. Ando, T. Matsuda, and 5. Sasaki, Chemtech, 1994–12, p. 20. Unfortunately, these materials are not photocurable.

U.S. Pat. No. 5,274,174 discloses a new class of photocurable compositions comprised of certain fluorinated monomers, such as diacrylates with perfluoro or perfluoropolyether chains, which possess low intrinsic absorption loss. It is, therefore, possible to make low loss optical interconnects from a photocurable system including these materials.

Fluorine substitution in the polymer structure, however, also induces some other less desirable changes in the polymer's physical properties. One such change is the decrease in refractive index. For a highly fluorinated acrylate photopolymer, the refractive index decreases to the 1.32 region when the H/F mole ratio reaches 0.25. For optical interconnect applications, to avoid loss of light, it is important that the refractive index of the core of a planar waveguide approximate and preferably match that of the optical fiber (generally 1.45). Another problem with fluorine substitution in the polymer is the decrease of the surface energy of the resulting photopolymer film which results in its reduced adhesion to other materials such as found in substrates.

It is also important to be able to precisely control and fine tune the refractive index of the photopolymer at the working wavelength in optical waveguide and interconnect applications. A desired index of refraction can be produced by mixing photocurable monomers with different refractive indices. Most photopolymers made from conventional photocurable monomers have refractive indices in the region of 1.45–1.55. Depending on the application, it is often desirable to lower a photopolymer's refractive index. One way to do this is to mix low refractive index fluorinated monomers with conventional hydrocarbon-based monomers. Unfortunately, this is difficult to accomplish because of the incompatibility or insolubility of the different monomer systems. Thus, there is a need for photocurable compositions which: (I) possess low optical loss in the near-infrared region, (II) possess a refractive index approaching traditional optical fibers; and (III) are compatible with both conventional hydrocarbon-based and highly fluorinated monomers.

BRIEF DESCRIPTION OF THE INVENTION

In accordance with the present invention, novel fluorine containing compounds are therefore provided which are suitable for use in optical devices such as fibers and waveguides. These novel compounds are readily radiation curable and curable by other means. These compounds are soluble with other components (cosolutes) and in numerous recoverable and re-useable solvents, and can be formulated to be of low viscosity when applied.

The novel fluorine containing compounds provide enhanced surface properties, and are fast curing but have indefinite pot life before exposure to radiation or other curing processes. The compounds, when cured, have a low refractive index. The compounds have good substrate adhesion, and can be chemically bonded into other resins, eliminating migratory problems associated with materials which are not bonded into a formulation, In addition, the compounds can be made from commercially available materials by both known and novel processes.

The compounds of the present invention are characterized by having one or more oxyvinyl groups separated from fluorine containing groups by at least one alkylene group having 1–8 carbon atoms and by at least one oxygen atom in addition to the oxygen on the oxyvinyl structure. More specifically, the compounds of the invention are oxyvinyl monoethers, oxyvinyl diethers, oxyvinyl monoesters and oxyvinyl diesters of fluorine containing structures.

In general the compounds of the invention have the generic formula:

$$R_z(L)_a(R_y)_b OROCH=CH_2.$$

Where L is =CHCOOROCH=CH$_2$; a is a number of 0 to about 1; R$_y$ is —CO—; b is a number of 0 to about 1; R is cycloalkane or (CH$_2$)$_x$—, where x is a number of about 2 through about 10; R$_z$ is R$_f$C$_n$H$_m$ where R$_f$ is a fluorinated alkylene moiety of about 1 to about 12 carbon atoms which may be linear or branch chained and may contain a further —OROCH=CH$_2$ group; n is an integer of about 1 through about 6; and m is an integer of n to 2n.

Fluorinated oxyvinyl monoethers of the invention may be characterized by the above generic formula where a and b are 0 and R$_z$ is free of additional oxyvinyl ether groups. The oxyvinyl monoethers may thus be represented by the formula:

R$_f$C$_n$H$_m$OROCH=CH$_2$.

Fluorinated oxyvinyl diethers of the invention may be characterized by the above generic formula where a is 0, b is 0, and R$_z$ contains another —OROCH=CH$_2$ group. The oxyvinyl diethers may thus be represented by the formula:

R$_f$C$_n$H$_m$[OROCH=CH$_2$]$_2$,

Fluorinated oxyvinyl monoesters of the invention may be characterized by the above generic formula where R$_y$ is —CO—, b is 1, and a is 0. The oxyvinyl monoesters may thus be represented by the formula:

R$_f$C$_n$H$_m$COOROCH=CH$_2$.

Fluorinated oxyvinyl diesters of the invention may be characterized by the above generic formula where a is 1 and b is 1. The oxyvinyl diesters may thus be represented by the formula:

R$_f$C$_n$H$_m$CH[COOROCH=CH$_2$]$_2$

The invention further includes novel methods of making the above compounds and uses of such compounds in coatings, inks, adhesives, structural polymers optical devices including fiber optics and wave guides, and to make photocured products using photocuring processes.

The invention further includes a novel method for making the fluorinated ester intermediates R$_f$C$_n$H$_m$CH[COOR]$_2$, used in making the fluorinated oxyvinyl monoesters and diesters of the invention., where R$_f$, C$_n$, H$_m$ and R are as previously described. R is preferably lower alkyl of about 1 to about 4 carbon atoms, e.g. methyl, ethyl, propyl, and butyl. The method comprises using a reaction solvent which is a mixture of tetrahydofuran (THF) and n-methylpyrrolidinone (NMP).

The invention also includes the novel intermediate R$_1$SO$_3$(R)CH=CH$_2$, used in making the fluorinated oxyvinyl monoethers and diethers of the invention, where R$_1$ can be alkyl, aryl or alkylaryl such as methyl, phenyl, or tolyl, where R$_1$ contains from about 1 to about 10 carbon atoms and R is as defined above.

DETAILED DESCRIPTION OF THE INVENTION

R$_f$ as used herein may be perfluorinated or partially fluorinated and may be linear or branch chained. R$_f$, in addition to containing hydrogen and fluorine, may contain other substitutions, such as an oxyvinyl ether group, as previously discussed. The R$_f$ group may additionally contain other halogen substitutions, especially chlorine or bromine, e.g. R$_f$ may be CX$_3$—(CF$_2$)$_c$—, where X is chlorine or bromine and c is about 1 to about 11. R$_f$ may also include one or more hydroxy, ether, ester, nitro, thio, mercapto, sulfo, heterocyclo, phenyl, substituted phenyl, cycloalkyl or substituted cycloalkyl groups. Specific examples of possible R$_f$ substituents are —OH, , —COOCH$_3$, —OCH$_3$, —OCH$_2$CH$_3$, NO$_2$, —SH, —SCH$_3$, phenyl, benzyl, cyclohexyl, and chlorocyclohexyl. In most cases, with the exception of halogen, the above substituents are attached to a non-fluorinated carbon atom of the R$_f$ group. Such substituents may also be attached to a C$_n$ or R carbon atom, provided that the substituent is not so electrophylic that it interferes with the stability of the oxyvinyl group. For that reason, the C$_n$ and R carbon atoms generally do not contain the highly electrophylic fluorine substituent.

The R group, as previously discussed, in addition to normal alkyl, may be branch chain, (still intended to be encompassed by the —(CH$_2$)$_x$— structural formula since the total number of carbon and hydrogen atoms remains constant whether the structure is linear or branched). The R group may also be cycloalkane, meaning that R may be cycloalkane alone or in conjunction with normal or branched alkane, e.g. cyclohexylmethyl.

The compounds of the invention may be made by a number of methods which form part of the present invention.

For example the fluorinated oxyvinyl ethers of the invention may be made by reacting an alkoxide of a fluorinated alcohol with a sulfonate vinyl ether of the formula R$_1$SO$_3$(R)OCH=CH$_2$ where R$_1$ and R are as defined above. The fluorinated alcohol may be either a monofunctional alcohol or a diol. When a monofunctional alcohol is reacted with one mole of the sulfonate vinyl ether, a mono functional fluorinated oxyvinyl ether is obtained. When a diol is reacted with two moles of the sulfonate vinyl ether, a fluorinated oxyvinyl diether is obtained.

Many suitable monofunctional alcohols may be defined by the formula R$_f'$(CF$_2$)$_x$C$_n$H$_m$OH, where R$_f'$ is —CF$_3$, —$CHF_2$, —$CH_2F$, or —$CH_3$ and x, n, and m are as previously defined. Specific examples of suitable commercially available fluorinated alcohols are:

1H,1H,8H,8H-dodecafluoro-1,8-octanediol, [$HOCH_2$ ;

2,2,3,3,4,4-hexafluoro-1,5-pentanediol, [$HOCH_2(CF_2)_3$ $CH_2OH$];

2,2,3,3,4,4,5,5-octafluoro-1,6-hexanediol, [$HOCH_2$ $(CF_2)_4 CH_2OH$];

1H,1H,10H,10H-hexadecafluoro-1,10-decanediol, [$HOCH_2(CF_2)_8CH_2OH$];

1H,1H,12H,12H-icosafluoro-1,12-dodecanediol, [$HOCH_2(CF_2)_{10}CH_2OH$];

octafluoropentanol, [$HCF_2CF_2CF_2CF_2CH_2OH$];

2,2,2trifluoroethanol, [$CF_3CH_2OH$]; and 1H,1H,7H-dodecafluoro-1-heptanol, [$CHF_2(CF_2)_5$ $CH_2OH$].

The reaction to form the fluorinated oxyvinyl ethers of the invention involves reacting the alkoxide of a fluorinated alcohol with the novel sulfonate alkyl vinylethers. The fluorinated alcohol alkoxides are prepared by reacting the alcohol with a base sufficiently strong to selectively deprotonate only the hydroxyl proton. Bases suitable for this reaction are the alkoxide bases of the alkali earth metals, preferably sodium or potassium, with the most preferred being sodium t-butoxide. Additionally, bases such as the alkali earth hydrides can also be employed with the most preferred being sodium hydride.

The novel sulfonate vinyl ethers for reaction with the fluorinated alkoxide may be described by the formula:

$$R_1SO_3(R)OCH=CH_2$$

and may be prepared by reacting commercially available hydroxyvinyl ethers with a base sufficiently strong to produce the alkoxyalkylvinyl ether, followed by subsequent reaction with an alkyl or arylsulfonyl chloride at a temperature conducive to result in the formation of the desired sulfonate vinyl ether intermediate.

The bases required for effecting the transformation to the alkoxyalkylvinyl ether can be the same as defined for the production of the fluorinated alcohol alkoxides, described above. Sodium t-butoxide and sodium hydride are the preferred bases. The most preferred base is sodium hydride.

The formation of either the fluorinated alcohol alkoxide or of the alkoxyalkylvinyl ether is performed at temperatures from −10 to 70° C., with the most preferred temperature being 10–20° C. In addition, to facilitate formation and dissolution, an inert solvent can be employed in the reaction. An inert solvent that can typically be used in the synthesis is tetrahydrofuran.

To prepare the sulfonate alkylvinyl ether it is necessary to perform the reaction at sufficiently low temperatures to avoid decomposition or undesired side reactions. Temperatures suitable for this synthesis range from −60 to 0° C. with the most preferred being −25 to −20° C. The reaction is performed by adding the alkyl or azyl sulfonyl chloride to the cooled preformed base of the alkoxyalkylvinyl ether solution. Typically, benzenesulfonyl chloride, toluenesulfonyl chloride or methanesulfonyl chloride can be used.

Once the alkylvinyl ether sulfonate has been formed it is rapidly added to the preformed fluorinated alcohol alkoxide solution. Formation of the desired fluorinated oxyvinyl ether is accomplished by heating the reaction mixture to between 70–80° C. for a period of time sufficient to complete the reaction, as determined by analyzing the reaction mixture by gas chromatography. This is normally achieved after 4–8 hours at reflux. Any reaction solvent that was utilized during the course of the reaction is removed by evaporation by conventional techniques followed by dissolving the remaining salts with water. The fluorinated oxyvinyl ether product separates from the water as a distinct phase and is isolated. Further purification of the product is accomplished by vacuum distillation.

---

Specific examples of fluorinated oxyvinyl ethers of the invention are:

$HCF_2(CF_2)_3CH_2O(CH_2)_4OCH=CH_2$;
$CF_3(CF_2)_2CH_2O(CH_2)_2OCH=CH_2$;
$CF_3CH_2O(CH_2)_4OCH=CH_2$;
$HCF_2(CF_2)_5CH_2O(CH_2)_4OCH=CH_2$;
$HCF_2(CF_2)_3CH_2O(CH_2)_2OCH=CH_2$;
$CF_3CH_2O(CH_2)_2OCH=CH_2$;
$CCl_3CH_2O(CH_2)_2OCH=CH_2$;

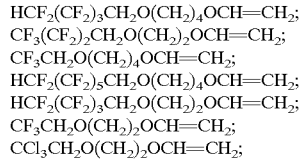

$CH_2=CHO(CH_2)_4OCH_2(CF_2)_6CH_2O(CH_2)_4OCH=CH_2$;
$CH_2=CHO(CH_2)_2OCH_2(CF_2)_6CH_2O(CH_2)_2OCH=CH_2$;

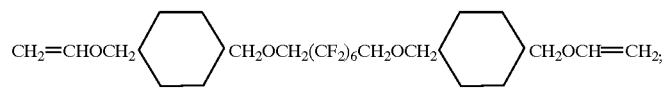

$HOCH_2(CF_2)_6CH_2O(CH_2)_4OCH=CH_2$;
$CH_3OCH_2(CF_2)_6CH_2O(CH_2)_4OCH=CH_2$;
$CH_3CH_2COOCH_2(CF_2)_6CH_2O(CH_2)_4OCH=CH_2$;
$HSCH_2(CF_2)_6CH_2O(CH_2)_4OCH=CH_2$;

Specific examples of fluorinated oxyvinyl ethers of the invention are:

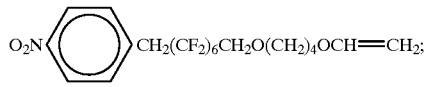

Examples of the intermediate sulfonate vinyl ethers of the invention are:

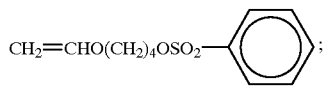

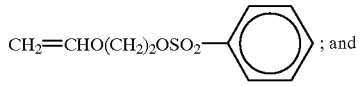

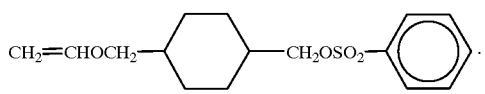

The oxyvinyl esters of the invention are prepared by reacting a carboxylic acid ester containing an active methylene group, e.g. dimethylesters of propanedioic acid, with a base which is sufficiently reactive to deprotenate at least one of the hydrogens from the activated methylene group. An active methyl group is one which will deprotenate in the presence of a strong base. The anion resulting from deprotenation is reacted with a suitable fluorine containing intermediate, e.g. a halogenated fluoroalkyl iodide to form a fluorinated ester compound which is then esterified with a hydroxyvinyl ether to form the fluorinated vinyl ether esters of the invention.

A diagram of a scheme to obtain fluorinated oxyvinyl esters of the invention is as follows:

$$ROOCCH_2COOR + base + R_fC_nH_mX \rightarrow R_fC_nH_mCH[COOR]_2$$

$$R_fC_nH_mCH[COOR]_2 + HO-(CH_2)_x-O-CH=CH_2 \rightarrow R_fC_nH_mCH[COOROCH=CH_2]_2$$

Where R, $R_f$, n, and m are as previously defined and X is chlorine, bromine or iodine.

The method for making the intermediate fluorinated ester compound $R_fC_nH_mCH[COOR]_2$ is unique and forms part of the present invention.

More specifically, in a preferred embodiment, propanedioic acid diesters, e.g. dimethyl and diethyl malonates, are reacted with a base which is sufficiently reactive to deprotenate at least one of the hydrogens from the activated methylene group. Typical of the bases envisioned in this patent are the alkoxides of the alkali earth metals, preferably sodium or potassium, with the most preferred being sodium t-butoxide.

Similarly, bases such as the alkali earth hydrides can also be employed, with the most preferred being sodium hydride.

The intermediate fluorinated esters are prepared by a modification of the procedure described by Smeltz et al. in U.S. Pat. No. 3,504,016. In that patent, the inventors describe a method for preparing fluorinated esters employing butanol as the solvent and sodium metal as the base. During the course of the reaction, copious quantities of precipitate form, rendering processing difficult. In addition, the mixed alcohol system results in the formation of mixed esters of the products.

Replacing the solvent system of U.S. Pat. No. 3,504,016 with a mixed solvent system consisting of tetrahydrofuran (THF) and n-methylpyrrolidinone (NMP) in approximately 80:20 weight percent, eliminates this problem. It is understood that this ratio may be varied, e.g. from about 60:40 to about 90:10 THF to NMP. Specifically, the solution remains homogeneous throughout the anion formation step and no cross esterification is observed. Pure products are isolated.

In addition to this improvement, the acid work up step of U.S. Pat. No. 3,504,016 can be eliminated. This is particularly advantageous as trace amounts of acid in this product would have disastrous affects in the transesterification with the vinyl ether compounds. In particular, rapid cross polymerization would occur this preventing product formation.

Fluorinated ester compounds, used as intermediates to make the fluorinated oxyvinyl esters of the invention, are prepared by reacting the above activated methyl group anion with a suitable fluorine containing starting material, usually a halogenated fluoroalkyl iodide of the general structure $R_fC_nH_mX$ where $R_f$ is a fluorinated alkyl group, as previously described, ; n is an integer of about 1 through about 6; m is an integer of n to 2n and X is chlorine, bromine or iodine. While the iodide derivative is the most preferred due to its rapid reactivity, the other halogen derivatives namely Cl and Br are also contemplated in this invention.

Halogens other than iodine may be especially desirable when chorofluoro compounds of the invention are made. As an example, a chlorofluoro compound of the invention can be made by the following scheme:

$$F_2C=CClF + BrCl_3C \rightarrow CCl_3(CF_2CFCl)_nBr$$

$$CCl_3(CF_2CFCl)_nBr + CH_2=CH_2 \rightarrow CCl_3(CF_2CFCl)nCH_2CH_2Br$$

This bromide can, for example, be substituted for the iodide as described above and in examples 11–20.

Reaction temperatures are not critical but are preferably conducted at the reflux temperature of tetrahydrofuran. The reactants employed in this process are readily available from commercial sources and are well known to those skilled in the art. It should also be apparent that by selecting the suitable reactant a variety of fluorinated esters can be prepared. In addition to the pure esters, the ester derived from the oligomeric mixture of fluorinated telomer iodides, commercially known as Zonyl TELB-L and sold by DuPont, can also be prepared. These fluorinated esters are required for the preparation of the vinyl ether esters of this invention.

The fluorinated vinyl ether esters of this invention are prepared by transesterifying the above fluorinated esters with a hydroxyvinyl ether of structure $$HO-(CH_2)_x-O-CH=CH_2$$

where x is about 2 to about 8 and encompasses methyl, ethyl and the like and cycloalkanes such as 1,4 cyclohexylmethylvinyl ether.

In the preferred practice of this invention, the fluorinated ester and hydroxyvinyl ether are combined in a 1:3 mole ratio for diester ethers and about 1:1.5 for monoester ethers. While these ratios are not critical and can be as low as 1:2 or greater than 1:3 for diester and as low as 1:1 or greater than 1:1.5 for monoesters, the 1:3 and 1:1.5 ratios provide for an effective reaction rate and high productivity of product. The reaction is preferably carried out in the presence of a catalyst, preferably titanium isopropoxide. While the amount of catalyst is not critical, effective reaction rates are achieved when the mole ratio of catalyst to fluorinated ester is at least $1 \times 10^{-3}$ to 1.

Similarly, the reaction temperature is not critical, but must be performed at an elevated value as compared to room temperature. The preferred temperature range is from 90–120° C. Reaction pressures are preferably maintained below atmospheric to assist in the rapid removal of methanol, a by product of this reaction. Preferably, the reaction pressure is maintained between 50 and 150 mmHg during the course of the reaction. The final products are isolated by conventional vacuum distillation.

---

Examples of the oxyvinyl esters of the present invention are:

$CF_3(CF_2)_5CH_2CH_2CH[CO_2(CH_2)_4OCH=CH_2]_2$;
$CCl_3(CF_2)_5CH_2CH_2CH[CO_2(CH_2)_4OCH=CH_2]_2$;
$CF_3(CF_2)_9CH_2CH_2CH[CO_2(CH_2)_4OCH=CH_2]_2$;
$CF_3(CF_2)_7CH_2CH_2CH[CO_2(CH_2)_4OCH=CH_2]_2$;
$CF_3(CF_2)_eCH_2CH_2CH[CO_2(CH_2)_4OCH=CH_2]_2$;

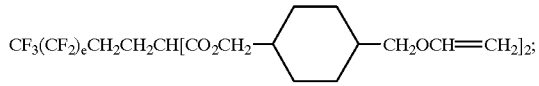

$CF_3(CF_2)_5CH_2CH_2CH[CO_2CH_3][CO_2(CH_2)_4OCH=CH_2]$;
$CF_3(CF_2)_7CH_2CH_2CH[CO_2CH_3][CO_2(CH_2)_4OCH=CH_2]$;
$CF_3(CF_2)_9CH_2CH_2CH[CO_2CH_3][CO_2(CH_2)_4OCH=CH_2]$; and
$CF_3(CF_2)_eCH_2CH_2CH[CO_2CH_3][CO_2(CH_2)_4OCH=CH_2]$, where e is a number of about 1 to about 12.

---

Examples of fluorinated ester intermediates used to prepare the fluorinated oxyvinyl esters of the invention are as follows:

$CF_3(CF_2)_5CH_2CH_2CH[CO_2CH_3]_2$;
$CF_3(CF_2)_7CH_2CH_2CH[CO_2CH_3]_2$;
$CF_3(CF_2)_9CH_2CH_2CH[CO_2CH_3]_2$; and
$CF_3(CF_2)_eCH_2CH_2CH[CO_2CH_3]_2$ The vinyl monomers of the invention contain much less hydrogen than conventional photocurable monomers such that their inherent carbon-hydrogen bond absorption is greatly reduced. In addition, the introduction of chlorine or bromine atoms into the molecule can offset the effect of fluorine on the refractive index of the monomer producing a material with an index of refraction between about 1.40–1.48. As a result, the monomers of the invention may be particularly useful in optical applications in the 1300–1550 nm wavelength region. The monomers are also compatible with both conventional hydrocarbon-based and highly fluorinated monomers. Because of this compatibility, it becomes possible to fine tune the refractive index and other physical properties of photocurable compositions containing these photocurable monomer.

The invention thus includes a photocurable composition comprising at least one photocurable monomer of the invention and a photoinitiator.

The invention also includes a process for producing an optical device containing a light transmissive region comprising: (a) applying a film of a photocurable composition comprising a photocurable monomer of the invention and a photoinitiator to a substrate; (b) imagewise exposing said composition to sufficient actinic radiation to form exposed and unexposed areas on the substrate; and (c) removing the unexposed portions of the composition.

In still another embodiment, the invention includes an optical device comprising a light transmissive region wherein said light transmissive region comprises a photocurable composition of the invention. Such optical devices include waveguides, splitters, routers, couplers, combiners, optical fibers and parts and combinations of such devices.

Such optical devices can be made by molding methods as described, for example, in U.S. Pat. No. 5,511,142. They can also be made by creating regions with differing degrees of polymerization and, as a consequence, different refractive indexes as described, for example, in U.S. Pat. No. 5,054,872. They can also be made through any combination of these methods or by other methods familiar to those skilled in the art of making optical devices.

The compounds of the invention are characterized by unique and useful properties, including excellent surface wetting, low surface tension, low friction and high slip, low flammability, high temperature resistance, low temperature resistance, low dielectric constant, nonstick surface characteristics, high chemical resistance, and excellent moisture resistance.

In addition to optical applications, the compounds of the invention find utility in numerous other areas, including, but not limited to, coatings, inks, moldings, photoresists, films, fibers, adhesives, insulators, and laminates. The compounds of the invention may be polymerized alone or with other vinyl or ethylenically unsaturated monomers, such as acrylates, other vinyl monomers and alkenes.

The following specific examples serve to illustrate and not limit the present invention. Unless otherwise indicated, all parts and percentages are by weight.

EXAMPLE 1

Preparation of Butylvinyl Ether Benzenesulfonate

Into a 3 L flask equipped with a mechanical stirrer and N2 purge was added 1000 g of tetrahydrofuran and 220.7 g (2.3 mol) of sodium t-butoxide. Hydroxybutyvinyl ether (236 g, 2.03 mol) was added dropwise at a rate to maintain the temperature at $\leq 40°$ C. This reaction mass was cooled to $-40°$ C. A solution of benzenesulfonyl chloride (353 g, 2 mol) in 300 g of tetrahydrofuran was added dropwise at a rate to maintain the reaction temperature at $\leq -20°$ C. After the addition was complete, the reaction mixture was allowed to warm to room temperature to obtain the butylvinyl ether benzenesulfonate,

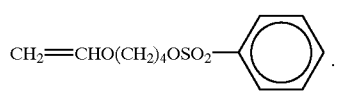

EXAMPLE 2

Preparation of Ethylvinyl Ether Benzenesulfonate

This compound was prepared in a manner similar to that described in Example 1 except that ethylene glycol vinyl ether (178.9 g, 2.03 mol) was used in the synthesis. This compound has the structural formula:

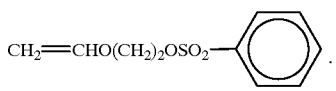

EXAMPE 3

Preparation of 1, 4-Cyclohexylmethylvinyl Ether Benzenesulfonate,

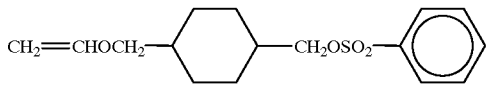

This compound was prepared in a manner similar to that described in Example 1 except that 1,4-cyclohexanedimethanol vinyl ether (398.5 g, 2.03 mol) was used in the synthesis.

EXAMPLE 4

Preparation of 5H—Octafluoropentane-oxybutylvinyl Ether
$HCF_2(CF_2)_3CH_2O(CH_2)_4OCH=CH_2$ Octafluoropentanol (487.4 g, 2.1 mol) was added dropwise to a suspension of sodium t-butoxide (203.8 g, 2.12 mol) in 500 g of tetrahydrofuran at a rate to maintain the reaction temperature at $\leq 25°$ C. After the addition was complete, the reaction content produced in Example 1 was added and the reaction heated to 80° C. for 8 hours. The solvent was then removed by distillation and the resulting solid dissolved in 3 L of water. The lower organic phase was separated and the product distilled at 54–58° C./0.4 mm to yield 508.3 g (77%).

EXAMPLE 5

Preparation of Heptafluorobutane-oxyethylvinyl Ether
$CF_3(CF_2)_2CH_2O(CH_2)_2OCH=CH_2$ This material was prepared as described in Example 4 except that 1H,1H-heptafluoro-1-butanol (424.1 g, 2.12 mol) and the reaction product from Experiment 2 was used. Yield of the product was 297.5 (82.5%). B.P.=77–80° C./50 mm.

EXAMPLE 6

Preparation of Trifluoroethyloxybutylvinyl Ether
$CF_3CH_2O(CH_2)_4OCH=CH_2$

This material was prepared as described in Example 4 except that 2,2,2-trifluoroethanol (900 g, 9 mol) was used. Yield of product which was distilled at 35–40° C./0.2 mm was 1488.11 g (84%).

EXAMPLE 7

Preparation of Dodecafluoroheptane-oxybutylvinyl Ether
$HCF_2(CF_2)_5CH_2O(CH_2)_4OCH=CH_2$ This compound was prepared as described in Example 4 except that 1H,1H,7H-dodecafluoro-1-heptanol (704 g, 2.12 mol) was used in the reaction sequence. Yield of product was 729 g (80%). B.P.=67–70° C./0.1 mm.

EXAMPLE 8

Preparation of 5H—Octafluoroventane-oxyethylvinyl Ether
$HCF_2(CF_2)_3CH_2O(CH_2)_2OCH=CH_2$ This compound was prepared as described in Example 4 except the alkoxyethyl vinyl ether prepared in Example 2 was used in the synthesis. Yield of product was 602 g (80%) based on a 2.5 mol scale.

The structure was confined by nmr and ir. B.P.=38–41° C./0.8–1 mm.

EXAMPLE 9

Preparation of Trifluoroethane-oxyethylvinyl Ether
$CF_3CH_2O(CH_2)_2OCH=CH_2$

This compound was prepared as described in Example 6 except that the reagent prepared in Example 2 was used in the synthesis (0.25 mol scale). Yield of product was 32 g (75%). B.P. —32–35° C./12 mm.

EXAMPLE 10

Preparation of Trifluoroethylcyclohexyl-dimethanol-monovinyl Ether,

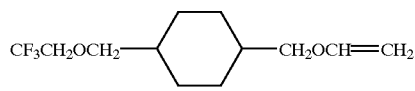

This compound was prepared as described in Example 6 except that the reagent prepared in Example 3 was used in the synthesis. Yield of the reaction based on a 1 mol scale was 200 g (72%). B.P. —56–60° C./0.5 mm.

EXAMPLE 11

Preparation of Propanedioic Acid, 1H,1H,2H,2H-Perfluorooctane-dimethyl Ester
$CF_3(CF_2)_5CH_2CH_2CH[CO_2CH_3]_2$ Sodium t-butoxide (22.1 g, 0.23 mol) was added to a solution of 120 mL of THF and 75 g of NMP. To this solution dimethylmalonate (27.77 g, 0.21 mol) was added at a rate to maintain the internal temperature at <65° C. Stirring was continued at this temperature for 30 minutes followed by the dropwise addition of 1-iodo-1H,1H,2H,2H-perfluorooctane (99.43 g, 0.21 mol). After the addition was complete, the reaction mixture was refluxed at 75–80° C. for two hours. The reaction was determined to be complete based on bas chromatograph analysis of the reaction mixture. The THF was removed at 120 mmHg/50° C. 150 mL of water was then added to the remaining reaction mass. The product phase separated. The crude product was distilled at 110–114° C./0.2 mmHg to yield 85 g (63% yield).

EXAMPLE 12

Preparation Propanedioic Acid, 1H,1H,2H,2H-Perfluorodecane-, Dimethyl Ester
$CF_3(CF_2)_7CH_2CH_2CH[CO_2CH_3]_2$ This material was prepared as described in Example 11 except that 1-iodo-1H,1H,2H,2H-perfluorodecane (99.3 g, 0.173 mo01) was substituted as a raw material. The crude product was distilled at 110–114° C./0.2 mm to yield 74 g (74% yield).

EXAMPLE 13

Preparation of Propanedioic Acid, 1H,1H,2H,2H-Perfluorododecane,-Dimethyl Ester
$CF_3(CF_2)_9CH_2CH_2CH[CO_2CH_3]_2$ This material was prepared as in Example 11 except that 1-iodo-1H,1H,2H,2H-perfluorododecane (250 g, 0.37 mol) was used as the starting material. The crude product was distilled at 160–175° C./0.1 mm to yield 193.2 g (77% yield). The product solidified upon cooling.

EXAMPLE 14

Preparation Propanedioic Acid, 1H,1H,2H,2H-α-Fluoropolydifluoromethylene,-Dimethyl Ester
$CF_3(CF_2)_nCH_2CH_2CH[CO_2CH_3]_2$ n=3,5,7,9 (mixture)

This material was prepared as described in Example 11 except that 1-iodo-1H,1H,2H,2H-α-fluoropolydifluoromethylene (553 g, 1 mol) was substituted as a raw material. The crude product was distilled at 150–160° C./0.2 mm to yield 445.6 g (80% yield).

EXAMPLE 15

Preparation of $CF_3(CF_2)_nCH_2CH_2CH[CO_2CH_3]_2$, using Propanedioic Acid, 1H,1H,2H,2H-α-Fluoropolydifluoromethylene,—Dimethyl Ester with Sodium Hydride as Base, n=3,5,7,9 (mixture)

The compound was prepared according to the procedure described in Example 11 except that NaH was substituted as base and the reaction was run on a 1 mol scale. Distillation afforded 420.7 g (76% yield).

EXAMPLE 16

Preparation of Propanedioic Acid, 1H,1H,2H,2H-Perfluorooctane-,dibutyvinyl Ether Ester
$CF_3(CF_2)_5CH_2CH_2CH[CO_2(CH_2)_4OCH=CH_2]_2$ Propanedioic acid, 1H,1H,2H,2H-perfluorooctane-—, dimethyl ester (85 g, 0.178 mol), hydroxybutylvinyl ether (62 g, 0.53 mol) and titanium tetraisopropoxide (0.081 g, 2.8×10⁻⁴ mol) were reacted at 110–112° C./50 mm to effect the transesterification reaction. After three hours, the formation of the by product, methanol, was complete. The product was isolated by vacuum distillation. The fraction boiling at 96–100° C./0.2 mm was identified as the product fraction. Yield=131.5 g (97%).

EXAMPLE 17

$CF_3(CF_2)_9CH_2CH_2CH[CO_2(CH_2)_4OCH=CH_2]_2$

The propanedioic ester product produced in Example 13 (100 g, 0.15 mol) was reacted with hydroxybutylvinyl ether (51 g, 0.45 mol) and titanium tetraisopropoxide (0.068 g, 2.4×10⁻⁴ mol) as described in Example 16. The product was isolated by distillation at 160° C./0.1 mm. Yield=111.7 g (88%).

EXAMPLE 18

$CF_3(CF_2)_7CH_2CH_2CH[CO_2(CH_2)_4OCH=CH_2]_2$

The propanedioic ester from Example 12 (230 g, 0.398 mol) was reacted with hydroxybutylvinyl ether (138.5 g, 1.19 mol) and titanium tetraisopropoxide (0.181 g, 6.3×10⁻⁴ mol) as described in Example 16. The product was isolated by distillation at 140–145° C./0.2 mm. Yield=289 g (97%).

EXAMPLE 19

$CF_3(CF_2)_nCH_2CH_2CH[CO_2(CH_2)_4OCH=CH_2]_2$, n=3,5, 7,9 mixture

The propanedioic ester oligomer mixture produced in Example 15 (420 g, 0.75 mol) was reacted with hydroxybutylvinyl ether (261 g, 2.25 mol) and titanium tetraisopropoxide (0.342 g, 1.2×10⁻³ mol) as described in Example 16. The product was isolated by distillation at 110–160° C./0.1 mm to yield 513.8 g (94%) of the bis(butylvinyl) ether fluorinated malonate.

EXAMPLE 20

n = 3, 5, 7, 9 mixture

The propanedioic ester oligomer produced in Example 15 (385 g, 0.69 mol) was reacted with cyclohexanol monovinyl ether (353.1 g, 2 mol) and titanium tetraisopropoxide (0.318 g, 1.11×10⁻³ mol) as described in Example 16. The product was isolated by distillation at 150–165° C./0.2 mm to yield 514.8 g (90%). This example illustrates the use of a cyclic vinyl ether in the synthesis.

EXAMPLE 21

Acrylate and vinyl ether polymers were made by UV polymerization of acrylate and vinyl ether monomers. Such polymers were prepared by homopolymerization without additives, and with non-reactive fluorochemical surfactant additive and by copolymerization with compounds of the present invention.

The resulting polymers were compared on the basis of surface fluorine, surface tension, blocking, release, bulk tensile properties and elongation.

The results are shown in the table.

Column 1 of the table gives the major resin composition in the polymer being tested.

The "acrylate" polymer comprised a cured mixture of 80 weight percent aliphatic urethane diacrylate oligomer, UCB Corporation trademark "Ehrecryl 8804"; 20 weight percent hexanediol diacrylate, and 2 parts per hundred (pph) of α,α dimethoxy-phenylacetophenone, free radical photocuring initiator, available under Ciba Geigy trademark "Irgaccure 651", plus additives shown in column 2 of the table.

The "acrylate" polymer was UV cured under nitrogen. At least about 200 millijoules (mJ)/cm² of UV exposure from a medium pressure mercury lamp was required for complete cure.

"FAVE" means fluorochemical oxyvinyl ether of the invention.

FAVE alone was cured using sulfonium hexafluoroantimonate photoinitiator, available from GE Corporation under the trademark GE-PI. Radiation exposure was about 400 mJ/cm² to cure.

"Vinyl Ether" in column 1 is a cured 50/50 combination of polyester divinyl ether oligomer, available from AlliedSignal, Inc. under the trademark VEX 1221 and 1,2-benzene carboxylic acid bis [4-(ethenyloxy) butyl] ester, available from AlliedSignal, Inc. under the trademark VE4010D. 0.5 pph of triaryl sulfonium salt of hexafluoro antimonate cationic photoinitiator was used. The photoinitiator is available from Sartomer Company, Inc. under the trademark CD1010. The vinyl ether was completely cured using about 400 mJ/cm² of UV radiation.

As shown in column 2 of the table, there was either no additive, FC430 fluorochemical surfactant additive, FC171 fluorochemical surfactant additive or a FAVE copolymerized additive of the invention. FC430 is a trademark of 3M Corporation for water soluble non-ionic fluoroaliphatic surfactant. FC171 is a trademark of 3M Corporation for slightly water soluble fluorochemical surfactant.

Column 3 of the table shows percent atomic fluorine at the top surface (TFS) by photoelectron spectroscopy based upon total carbon, nitrogen, oxygen, fluorine, and silicon.

Column 4 shows percent atomic fluorine at the bottom surface, (BFS).

Column 5 shows percent top surface atomic fluorine after 20+rubs with methyl ethyl ketone (MEK) for the acrylate and 100% FAVE polymer coatings and 4+rubs with MEK for the vinyl ether polymer coatings.

Column 6 shows percent top surface atomic fluorine after being postcured at 80° C. for 15 minutes and after 20+rubs with methyl ethyl ketone for polyacrylate and 4+rubs for polyvinyl ether.

Column 7 shows surface tension in dynes/cm.

Column 8 shows block separation force between top surfaces using 44 grams per square inch block forming pressure. Block separation force is force in grams to peel back a blocked section of one half inch width at 1.5 inches per minute.

Column 9 shows force of release of adhesive tape from the top surface at 12 inches per minute. The tape used was 3M Corporation 810 adhesive tape.

Columns 10 and 11 show tensile strength using the Youngs Modulus in Ksi. "Ksi"=1000 psi and stretch characteristics using percent elongation.

This example illustrates the resulting effect on surface energy by adding various load levels of the fluorinated oxyvinyl ethers of this invention into standard acrylate formulations and into standard vinyl ether formulations used by those in the industry. As can be seen, the addition of the fluorinated vinyl ethers has a dramatic effect in reducing the surface tension in both the neat liquid and the cured film at even the 0.1 wt % level. The lower surface tension in the liquid state as compared to the patent formulation indicates that these fluids will have an improved surface wetting property. Similarly, the decrease in surface energy of the polymerized film indicates that these materials will exhibit low surface tension, low friction and non-stick surfaces.

This example further demonstrates the non-fugitive properties of the vinyl ethers of this invention in acrylate and vinyl ether polymer compositions. It compares the vinyl ethers of the invention to commercially available fluorinated surfactants used in the art. As can be observed, after performing the industry standard test of MEK double rubs, polymerized films containing the fluorinated surfactant additives significantly decrease in percent surface content of fluorine as compared to the fluorinated materials of this invention. This substantiates the non-fugitive nature of the materials of the invention as compared to current art materials, as well as demonstrating that materials formulated and polymerized with the fluorinated ethers will exhibit extended wear performance, resistance and the like. The higher surface fluorine content of compounds of the invention, coupled with its steady state value as compared to the decreasing value observed with the fluorinated surfactant series of fluorinated additives, demonstrate improvements over prior art technology.

The results of this example further demonstrate that the oxyvinyl ethers of the invention can be used both in acrylate based polymers by free radical polymerization and in vinyl ether based polymers by cationic polymerization.

Materials of these compositions will impart improved wear, temperature resistance and chemical resistance, just to indicate a few enhanced properties. Such properties can thus be enhanced by use of the compounds of the invention in many areas such as: coatings, plastics, inks, moldings, adhesives and optical devices.

TABLE

CORRELATION OF SURFACE FLUORINE WITH SURFACE TENSION, BLOCKING, RELEASE, BULK TENSILE PROPERTIES AND ELONGATION

| Major Resin | Additive | TFS Atomic Fluorine | BFS Atomic Fluorine | TFS after MEK | TFS after MEK Postcure | Surface Tension of Cured film Top | Surface Tension of Liquid | Top to Top Blocking Grams | Release Grams | Tensile Youngs Modulus (Ksi) | % Elongation at Break |
|---|---|---|---|---|---|---|---|---|---|---|---|
| Example 19 FAVE | None | 34.42 | 31.6 | 35.42 | 33.3 | | | | | | |
| Acrylate 100% | None | 0 | 0 | 0 | 0 | 42 | 51 | 5 | 626 | 56 | 31 |
| Acrylate | 0.1 pph Example 19 FAVE | 8 | 0 | 6.1 | 7.1 | 32 | 46.9 | 2.6 | 611 | | |
| Acrylate | 0.5 pph Example 19 FAVE | 15.3 | 0.6 | 13.9 | 14 | <30 | 42.2 | 1.4 | 350 | 54 | 31 |
| Acrylate | 0.1 pph FC-430 | 1.7 | 0.5 | 0.7 | 1.1 | 38 | 41.4 | 3.9 | 560 | | |
| Acrylate | 0.5 pph FC-430 | 6.7 | 0.69 | 1.8 | 5.5 | 36 | 35.5 | 2.5 | 465 | 51 | 34 |
| Acrylate | 0.1 pph FC-171 | 9.8 | 9.3 | 4.1 | 8.5 | 36 | 37.4 | 2.7 | 673 | | |
| Acrylate | 0.5 pph FC-171 | 15.6 | 11.4 | 10.9 | 16.9 | 34 | 32.6 | 1.4 | 675 | 47 | 29 |
| Acrylate | 0.5 pph Example 16 FAVE | 9 | 0.3 | 7.5 | 7.9 | 30 | 40.2 | 2.3 | 493 | 45 | 40 |
| Acrylate | 0.5 pph Example 8 FAVE | o.5 | 0.1 | 0.2 | 0.3 | 42 | 41.7 | 4.1 | 608 | 43 | 37 |

TABLE-continued

CORRELATION OF SURFACE FLUORINE WITH SURFACE TENSION, BLOCKING, RELEASE, BULK TENSILE PROPERTIES AND ELONGATION

| Major Resin | Additive | TFS Atomic Fluorine | BFS Atomic Fluorine | TFS after MEK | TFS after MEK Postcure | Surface Tension of Cured film Top | Surface Tension of Liquid | Top to Top Blocking Grams | Release Grams | Tensile Youngs Modulus (Ksi) | % Elongation at Break |
|---|---|---|---|---|---|---|---|---|---|---|---|
| Vinyl Ether | None | 0 | 0 | 0 | 0 | 744 | 36.6 | 345 | 611 | 115.7 | 30.3 |
| Vinyl Ether | 0.5 pph FC-430 | 9.83 | 1.47 | 2.67 | 3.36 | 34 | 30 | 2.3 | 388 | 153.2 | 14.3 |
| Vinyl Ether | 0.5 pph FC-171 | 12.95 | 1.12 | 1.59 | 4.6 | 34 | 29.3 | 3.2 | 604 | 141.2 | 22.2 |
| Vinyl Ether | 0.5 pph Example 19 FAVE | 17.2 | 0.2 | 15.9 | 17.2 | <30 | 36 | | | | |
| Vinyl Ether | 1.0 pph Example 19 FAVE | 21.74 | 0.54 | 20.2 | 20.81 | <30 | 28 | 2.7 | 242 | 134.7 | 26.2 |
| Vinyl Ether | 2.5 pph Example 19 FAVE | 25.65 | 1.23 | 24.63 | 25.31 | <30 | 26.3 | 0.86 | 196 | 131.7 | 25.2 |
| Vinyl Ether | 5 pph Example 19 FAVE | 27.85 | 1.96 | 28.57 | 29.89 | <30 | 25.2 | 1.0 | 160 | 136.8 | 24.4 |

We claim:

1. A compound having the formula:

$$R_z(L)_a(R_y)_b OROCH=CH_2$$

where L is =CHCOOROCH=CH$_2$; a is 0 to about 1; $R_y$ is —CO—; b is a number of 0 to about 1; R is cycloalkane or $(CH_2)_x$—, where x is a number of from about 2 to about 10; $R_z$ is $R_fC_nH_m$ where $R_f$ is a fluorinated alkylene moiety of from about 1 to about 12 carbon atoms; n is an integer of from about 1 to about 6; and m is an integer of from n to 2n provided that when R is CH$_2$ and a and b=0, x is at least 4 to about 10.

2. The compound of claim 1 wherein $R_f$ is linear chained.

3. The compound of claim 1 wherein $R_f$ of $R_z$ further contains an —OROC=CH$_2$ group.

4. The compound of claim 1 wherein $R_f$ of $R_z$ further contains at least one halogen selected from the group consisting of chlorine and bromine.

5. The compound of claim 1 wherein $R_f$ of $R_z$ further contains at least one group selected from the group consisting of —OH, —COOCH$_3$, —OCH$_3$, —OCH$_2$CH$_3$, —NO$_2$, —SH, —SCH$_3$, phenyl, benzyl, cyclohexyl and chlorocyclohexyl.

6. A fluorinated oxyvinyl monoether of claim 1 where a and b are 0.

7. A fluorinated oxyvinyl diether of claim 1 where a is 0, b is 0, and $R_z$ contains at least one —OROCH=CH$_2$ group.

8. A fluorinated oxyvinyl monoester of claim 1 where b is 1, and a is 0.

9. A fluorinated oxyvinyl diester of claim 1 where a is 1 and b is 1.

10. An oxyvinyl ether selected from the group consisting of:

HCF$_2$(CF$_2$)$_3$CH$_2$O(CH$_2$)$_4$OCH=CH$_2$;
CF$_3$CH$_2$O(CH$_2$)$_4$OCH=CH$_2$;
HCF$_2$(CF$_2$)$_5$CH$_2$O(CH$_2$)$_4$OCH=CH$_2$;
CCl$_3$CH$_2$O(CH$_2$)$_2$OCH=CH$_2$;

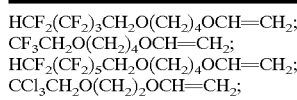

CH$_2$=CHO(CH$_2$)$_4$OCH$_2$(CF$_2$)$_6$CH$_2$O(CH$_2$)$_4$OCH=CH$_2$;
CH$_2$=CHO(CH$_2$)$_2$OCH$_2$(CF$_2$)$_6$CH$_2$O(CH$_2$)$_2$OCH=CH$_2$;

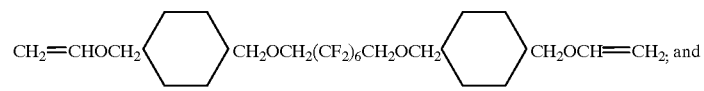

HOCH$_2$(CF$_2$)$_6$CH$_2$O(CH$_2$)$_4$OCH=CH$_2$.

11. A fluorinated oxyvinyl ester selected from the group consisting of:

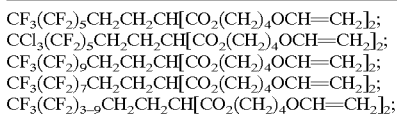

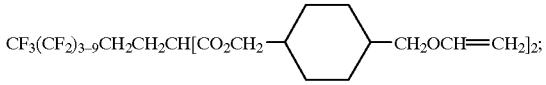

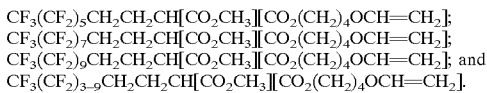

12. A method for preparing an oxyvinyl ether compound of claim 1 comprising reacting an alkoxide of a fluorinated alcohol with a sulfonate vinyl ether of the formula $R_1SO_3(R)OCH=CH_2$, where $R_1$ is alkyl of from about 1 to about 10 carbon atoms and R is cycloalkane or $(CH_2)_x$ where x is from about 2 to about 10.

13. The method of claim 12 wherein the fluorinated alcohol has the formula $R_f'(CF_2)_xC_nH_mOH$, where $R_f'$ is —$CF_3$, —$CHF_2$, —$CH_2F$, or —$CH_3$ and x is from about 2 to about 10, n is from about 1 to about 6, and m is a number of from n to 2n.

14. A method for the preparation of a fluorinated oxyvinyl ester compound according to claim 1 comprising:

a) reacting a carboxylic acid containing an active methylene group with a base which is sufficiently reactive to deprotenate at least one of the hydrogens from the activated methylene group;

b) reacting the resulting anion with a fluoroalkyl halide to form a fluorinated ester compound; and c) esterifying the fluorinated ester compound with a hydroxyvinyl ether to form the fluorinated oxyvinyl ester.

15. The method of claim 14 wherein the carboxylic acid containing an active methylene group has the formula $ROOCCH_2COOR$.

16. A method for the preparation of a fluorinated ester compound of the formula $R_fC_nH_mCH[COOR]$ where $R_f$ is a fluorinated alkylene moiety of from about 1 to about 12 carbon atoms which may be linear or branch chained, n is a number of from about 2 to about 6, m is a number of n to 2n, and R is cycloalkane or $(CH_2)_x$ where x is about 2 to about 10; said method comprising:

a) reacting a carboxylic acid ester of the formula $ROOCCH_2COOR$ containing an active methylene group with a base which is sufficiently reactive to deprotenate at least one of the hydrogens from the activated methylene group; and b) reacting the resulting anion with a fluoroalkyl halide of the formula $R_fC_nH_mX$ in a solvent comprising a mixture of tetrahydrofuran and n-methylpyrrolidinone to form the fluorinated ester compound.

17. A fluorinated oxyvinyl diester of claim 1 where a is 1 and b is 0.

* * * * *